(12) United States Patent
Takashima

(10) Patent No.: US 7,509,867 B2
(45) Date of Patent: Mar. 31, 2009

(54) BIOINFORMATION DETECTION DEVICE UTILIZING AIR PRESSURE VARIATION

(75) Inventor: Mitsuru Takashima, Tokyo (JP)

(73) Assignee: M. I. Laboratories Corporation, Tokyo (JP)

( * ) Notice: Subject to any disclaimer, the term of this patent is extended or adjusted under 35 U.S.C. 154(b) by 758 days.

(21) Appl. No.: 10/503,379

(22) PCT Filed: Feb. 4, 2003

(86) PCT No.: PCT/JP03/01126

§ 371 (c)(1),
(2), (4) Date: Sep. 13, 2004

(87) PCT Pub. No.: WO03/065892

PCT Pub. Date: Aug. 14, 2003

(65) Prior Publication Data

US 2005/0092812 A1    May 5, 2005

(30) Foreign Application Priority Data

Feb. 5, 2002   (JP) .............................. 2002-028116

(51) Int. Cl.
*G01L 9/04*    (2006.01)

(52) U.S. Cl. .......................... 73/720; 73/715; 361/283.1
(58) Field of Classification Search ........... 73/700–756; 361/283.1–283.4
See application file for complete search history.

(56) References Cited

U.S. PATENT DOCUMENTS

| | | | | |
|---|---|---|---|---|
| 3,651,697 A | * | 3/1972 | Ianuzzi .......................... | 73/714 |
| 4,768,382 A | * | 9/1988 | Varrese ......................... | 73/715 |
| 5,107,710 A | * | 4/1992 | Huck et al. .................... | 73/708 |
| 6,229,427 B1 | * | 5/2001 | Kurtz et al. .................... | 338/42 |
| 6,447,342 B1 | * | 9/2002 | Lawlyes et al. .............. | 439/686 |
| 7,077,009 B2 | * | 7/2006 | Lokhorst et al. .............. | 73/745 |

* cited by examiner

*Primary Examiner*—Andre J Allen
*Assistant Examiner*—Jermaine Jenkins
(74) *Attorney, Agent, or Firm*—Robert D. Katz, Esq.; Cooper & Dunham LLP

(57) ABSTRACT

A bioinformation detection device, comprising a three-layer structure having a base, an elastic body, and a cover body, wherein a closed space is formed by a load applied to the structure, a strain detection element is sealed in the closed space, and an air pressure variation caused by bioinformation is converted into an electric signal and taken out, whereby the detail bioinformation can be accurately provided for a long time.

12 Claims, 4 Drawing Sheets

US 7,509,867 B2

BIOINFORMATION DETECTION DEVICE UTILIZING AIR PRESSURE VARIATION

TECHNICAL FIELD

This invention relates to a device for detection of bioinformation, and particularly to such a device relying on changes in pneumatic pressure under the biological load for bioinformation detection. More particularly, the invention pertains to a device including a hollow, open-top pedestal, complete with a load-sensing cap, in which there is mounted a strain sensor for sensing changes in pneumatic pressure due to the biological load exerted via a leg of a bed, chair, or the like on the load-sensing cap. The term "strain sensor" should be construed to mean any device capable of sensing strain, as by generating a voltage or varying in electrical resistance, examples being a piezoelectric element, strain gage, and semiconductor sensor.

The usual conventional practice for measurement of biological parameters such pulse, breathing, and bodily movements has been to affix electrodes or probes to the humans or animals. The signals picked up by these devices are sent over cables or cords to the associated instruments for measurement or observation.

This conventional practice is objectionable in that the electrodes or probes are easy to be displaced on or detached from the human or animal bodies while in use, failing to pick up the signals from where they should. Another objection is that the connecting wires such as cords are susceptible to breakage under certain circumstances of usage, as at their intersections or folds under the bedding. The breaking of the connecting wires may lead to the danger of electrification as when the instrument is powered from a commercial power supply. What is more, the connecting wires lend themselves to undesired functioning as antennas, attracting external electromagnetic noise.

There has been a known method of bioinformation measurement other than the attachment of electrodes or probes to human or animal bodies. It employs an air-filled bag or mat laid, for example, under part or whole of the recumbent human body. Pressure variations created inside the bag or mat are detected with pressure sensors.

Although free from the shortcomings of the first recited prior art, this alternative method possesses the drawback that the air bag or mat must be much larger than the human body, or two or more bags or mats put to joint use, in order to allow for some body movements thereon. It is also a serious demerit of this alternative method that the air bags or mats are themselves so elastic that they absorb pressure variations thereon. These devices are therefore unfit for applications where very fine signals must be handled.

DISCLOSURE OF INVENTION

The present invention seeks to accurately detect all the required bioinformation from both humans and animals as they lie on a bed, chair or the like, without need for attachment of probes or the like to the bodies or for provision of outsize air bags or mats.

For the attainment of these objects, the present invention proposes a bioinformation detector having a pedestal and a cap thereon which in combination define an enclosed space accommodating a strain sensor. The detector is designed to be placed under a leg of a bed, chair or the like, where the weight of the biological body concentrates. The desired bioinformation is collected by detecting changes in the pressure of the enclosed space by the strain sensor.

BEST MODE FOR CARRYING OUT THE INVENTION

Figure 1:
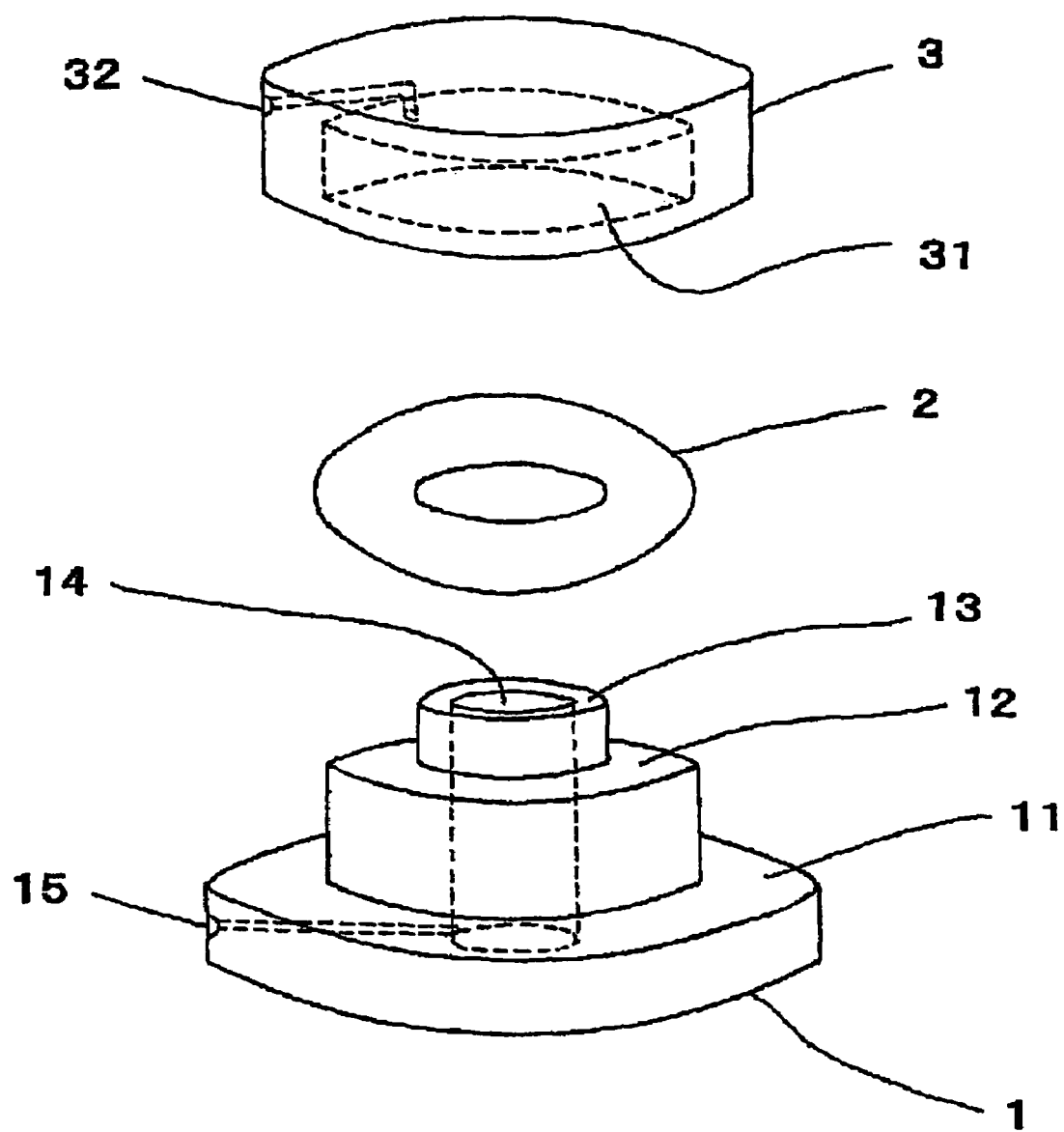
FIG. 1 is an exploded perspective view of the bioinformation detector embodying the novel concepts of this invention.

The mechanical organization of the bioinformation detector according to the invention will be apparent from a study of FIG. 1, from which electrical parts have been omitted for simplicity. The reference numeral 1 in this figure generally denotes a pedestal in the shape of an up-standing, hollow, open-top cylinder, complete with three annular steps 11, 12 and 13 to provide three coaxial cylindrical parts which diminish in diameter from the bottom upwards.

The pedestal 1 defines a cavity 14 extending coaxially from the top of the pedestal and terminating short of its bottom. Although shown to be cylindrical in shape, the cavity 14 could be of various other shapes as long as they do not run counter to the constructional and operational features of the bioinformation detector hereinafter set forth.

The pedestal 1 is furnished with means 15 for adjustment of static air pressure in the cavity 14. The pressure adjustment means 15 include an air passageway extending radially of the pedestal 1 to communicate the cavity 14 with atmosphere. The air passageway is equipped with valve means for placing the cavity 14 in and out of communication with atmosphere as well as for permitting controlled airflow through the passageway for optimum static pressure.

FIG. 1 also shows a sealing ring of elastic material with a circular cross-sectional shape. The sealing ring 2 has an inside diameter approximately equal to the inside diameter of the pedestal step 12, and an outside diameter approximately equal to its outside diameter. The sealing ring 2 can therefore fit over the step 13 so as to rest on the step 12.

Shown also in FIG. 1 is a cap 3 having a cavity 31 extending upwardly from its bottom and terminating short of its top. The cap cavity 31 has a diameter somewhat greater than the outside diameter of the pedestal step 12. The cap 3 is also provided with an air passageway and associated valve means 32 for placing the cap cavity 31 in and out of communication with atmosphere, with a capability of permitting airflow through the passageway at a controlled rate for optimization of static air pressure in the cap cavity.

Figure 2:
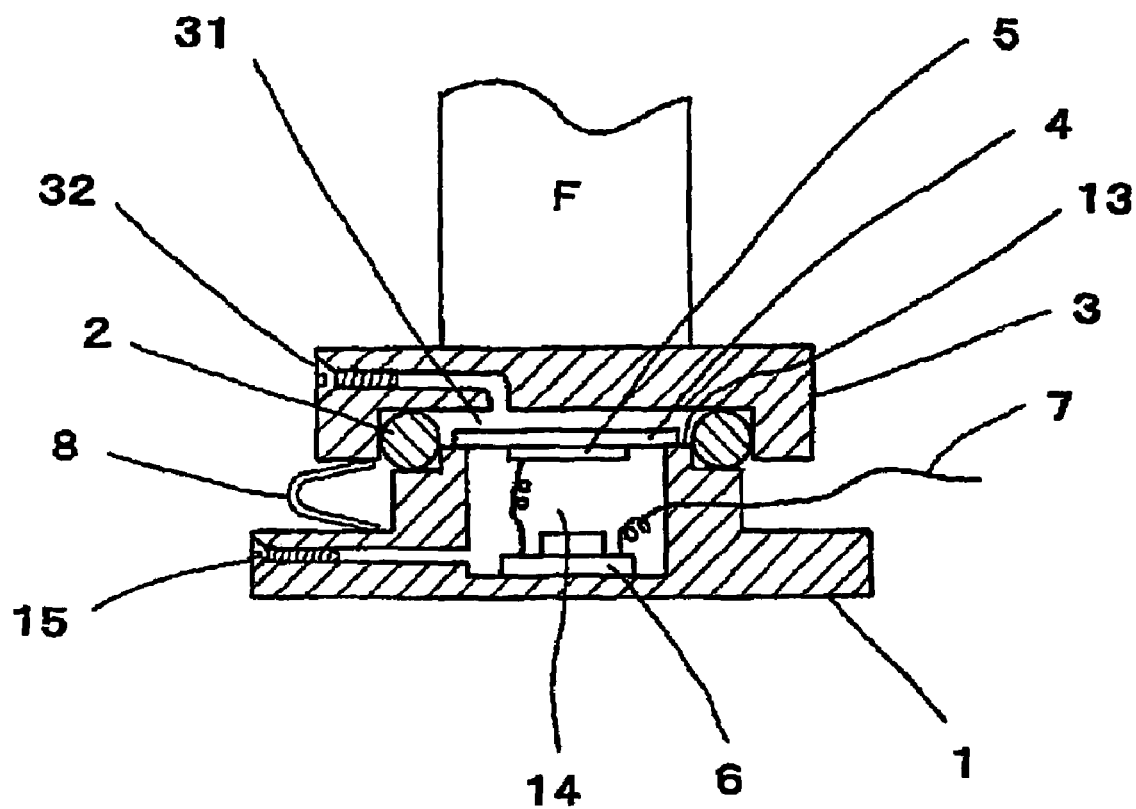
FIG. 2 is an axial section through the bioinformation detector of FIG. 1 assembled and fitted with electric means.

FIG. 2 depicts the pedestal 1, sealing ring 2, and cap 3 of FIG. 1 assembled together with some additional means to provide the bioinformation detector according to the invention. The pedestal 1 has its open top dosed by a diaphragm 4 which has its peripheral marginal edge affixed to the step 13. A strain sensor 5 is attached to the underside of the diaphragm 14 and electrically connected to a circuit board 6 on the bottom of the pedestal cavity 14. The circuit board 6 is furnished with means for amplifying the signal generated by the strain sensor 5, preparatory to delivery to external circuitry, not shown, by way of a cable or cord 7. Wireless sensor signal transmission is of course possible by incorporating a power supply and transmitter with the circuit board 6.

A conductor or conductors 8 are installed between pedestal 1 and cap 3 for electrostatically shielding the pedestal cavity 14 and cap cavity 31. Preferably, the conductors 8 may be made from resilient material in order to add to resiliency between pedestal 1 and cap 3.

When a leg F of a bed or chair is placed on this bioinformation detector as in FIG. 2, the sealing ring 2 will yield to the weight exerted thereon via the cap 3, thereby hermetically sealing the joint between pedestal 1 and cap 3 and hence the cap cavity 31 above the diaphragm 4. The physical vibration transmitted from the human or other biological entity on the bed or bed to the cap 3 will cause pressure variations in the hermetically closed space. The strain sensor 5 will translate the resulting strain of the diaphragm 4 into a voltage signal. Received and amplified by the electronic circuit on the circuit board 6, the sensor output signal will be delivered over the cable 7 to the unshown external means for measurement or observation.

The static air pressures in the pedestal cavity 14 and cap cavity 31 may be independently adjusted and optimized as aforesaid by the pressure adjustment means 15 and 32. For instance, if the load weight from the leg F is found excessive, the adjustment means 32 on the cap 3 may be opened to permit air escape from the cap cavity 3 until the pressure drops to a desired degree. The pressure in the pedestal chamber 14 may be made equal to the atmospheric pressure by opening the pressure adjustment means 15 if the load weight is too light.

Notwithstanding the showing of FIG. 2, and as will have been understood from the foregoing, the bioinformation detector according to the invention need not necessarily be positioned in use with the cap 3 directed upward. It will indeed function just as well if placed upside down, with the leg F loaded on the pedestal 1. Desired bioinformation will be obtained equally well if the device is positioned either way.

Figure 3:
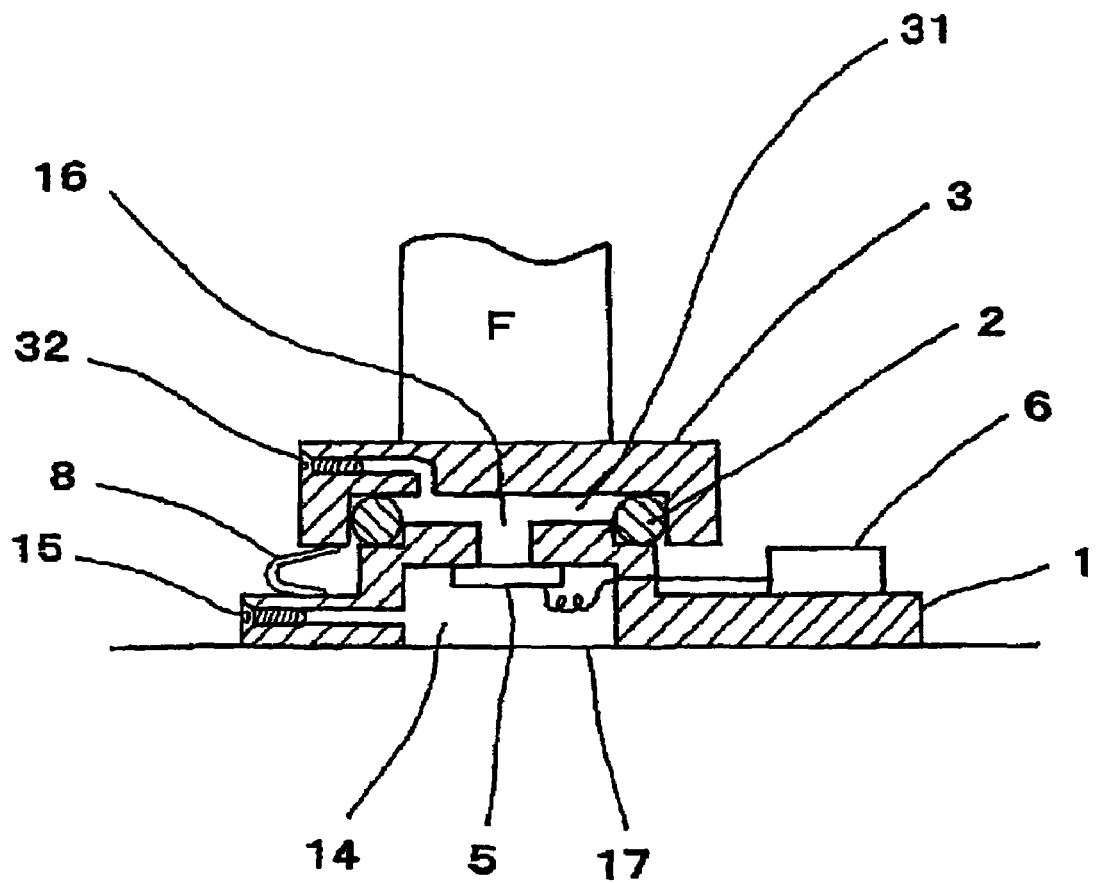
FIG. 3 is a view similar to FIG. 3 but showing another preferred form of bioinformation detector according to the invention.

Another preferred embodiment of the invention is shown in FIG. 3, in which parts corresponding to those in FIGS. 2 and 3 are identified by like reference characters. This second embodiment includes the pedestal 1 with a modified cavity 14 having a constriction 16 open to the cap cavity 31. The other end, at the bottom of the pedestal 1, is open but is closed as the pedestal 1 is positioned on the floor 17.

The constriction 16 makes it unnecessary to close the open top of the pedestal cavity 14 with a diaphragm as in the previous embodiment; instead, the strain sensor 5 is mounted directly to the top of the pedestal 1 so as to close the constriction 16 of the pedestal cavity 14.

Thus the pressure variations caused in the cap cavity 31 will be applied directly to the strain sensor 6 via the constriction 16 thereby straining the strain sensor 6 and so causing the latter to develop a proportional voltage signal. The voltage signal will be amplified by the unshown amplifier on the circuit board 6, which is shown mounted to the outside of the pedestal 1, preparatory to delivery to the external equipment for measurement or observation. As in the previous embodiment, such signal delivery to the external equipment may be made without use of wires, by incorporating a battery and transmitter with the circuit board 6. The pressure adjustment means 15 and 32 are of the same construction and operation as their counterparts of the foregoing embodiment.

Figure 4:
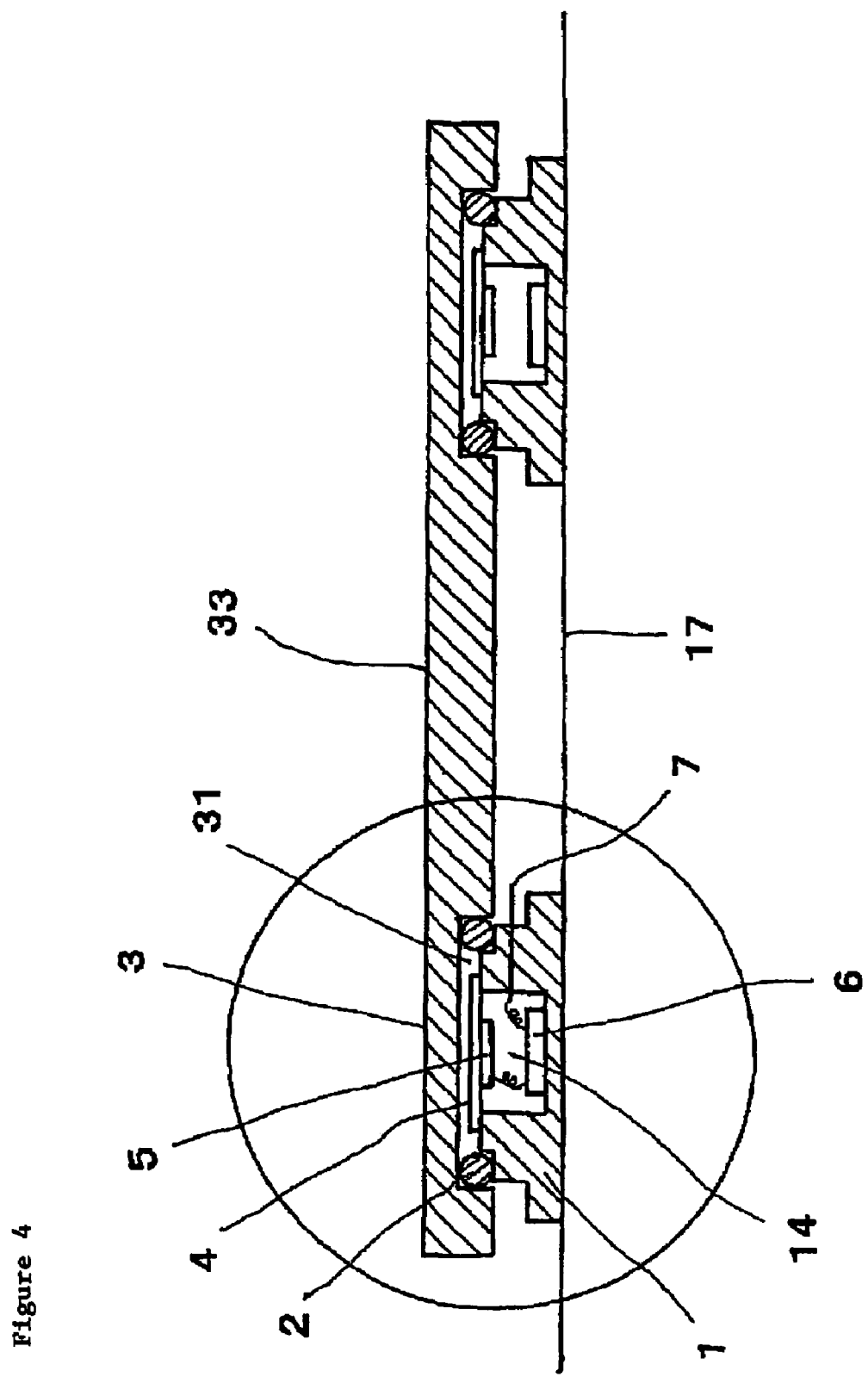
FIG. 4 is a vertical section through still another preferred form of bioinformation detector incorporating a plurality of detector units each constructed ass in FIGS. 1 and 2.

Two or more bioinformation detectors according to the invention, each constructed as in FIG. 2 or 3, may be put to combined use as in FIG. 4. Desired bioinformation will be obtained satisfactorily if only one device of the FIG. 2 or 3 construction is placed under one of the four legs of a bed or chair. Actually, however, such devices will have to be placed under all the legs because the bed or chair would slant or become rickety if only one is installed under one of its legs. It must also be taken into consideration that the weight of the object of measurement will be distributed over large areas if it lies on something that has no legs or like downward projections, such as a toilet seat, bathtub, or flooring. The embodiment of FIG. 4 is well adapted for such applications.

The part of the composite apparatus shown encircled in FIG. 4 is of exactly the same construction as the bioinformation detector of FIG. 2 except that the pressure adjustment means 15 and 32 are not shown for simplicity. The caps of all the individual detector units of FIG. 4 are integrally combined into what may be termed a platform 33. This platform is subject to change in both shape and size depending upon what is to be placed thereon, for example, a bed, chair, toilet seat, and so forth. The subject of measurement may lie directly on the platform 33, either recumbently or otherwise.

As has been mentioned in connection with FIG. 2, the individual detector units of FIG. 4 could be positioned upside down. In that case the pedestals 1, instead of the caps 3, of all the detector units might be combined into one platform.

INDUSTRIAL APPLICABILITY

The bioinformation detector according to the invention is applicable to medical and healthcare fields, by being compactly attached to the legs of beds or chairs, toilet seats, or floorings for accurately capturing information from the biological objects resting thereon.

The invention claimed is:

1. A bioinformation detector comprising:
   (a) a pedestal including an open-top pedestal cavity;
   (b) a diaphragm closing the open top of the pedestal cavity;
   (c) a cap mounted on the pedestal, the cap defining a cap cavity open to the diaphragm;
   (d) a resilient member installed between the pedestal and the cap for hermetically sealing a joint therebetween when the cap is loaded with an object for bioinformation detection; and
   (e) a strain sensor attached to the diaphragm for sensing changes in air pressure in the hermetically sealed space.

2. A bioinformation detector as set forth in claim 1, further comprising pressure adjustment means for adjustably varying static air pressure in the pedestal cavity.

3. A bioinformation detector as set forth in claim 1, further comprising pressure adjustment means for adjustably varying static air pressure in the cap cavity.

4. A bioinformation detector as set forth in claim 1, further comprising a conductor coupled between the pedestal and the cap.

5. A bioinformation detector as set forth in claim 1, further comprising a conductor of resilient material installed between the pedestal and the cap.

6. A bioinformation detector comprising a plurality of bioinformation detector units each constructed as in claim 1, and a platform formed by integrally joining caps of all of the bioinformation detector units.

7. A bioinformation detector comprising:
   (a) a pedestal including a pedestal cavity having a constriction;
   (b) a cap mounted on the pedestal, the cap defining a cap cavity open to the constriction of the pedestal cavity;

(c) a resilient member installed between the pedestal and the cap for hermetically sealing a joint therebetween when the cap is loaded with an object of bioinformation detection; and (d) a strain sensor mounted to the pedestal so as to close the constriction of the pedestal cavity for sensing changes in air pressure in the hermetically sealed space.

8. A bioinformation detector as set forth in claim 7, further comprising pressure adjustment means for adjustably varying static air pressure in the pedestal cavity.

9. A bioinformation detector as set forth in claim 7, further comprising pressure adjustment means for adjustably varying static air pressure in the cap cavity.

10. A bioinformation detector as set forth in claim 7, further comprising a conductor coupled between the pedestal and the cap.

11. A bioinformation detector as set forth in claim 7, further comprising a conductor of resilient material installed between the pedestal and the cap.

12. A bioinformation detector comprising a plurality of bioinformation detector units each constructed as in claim 7, and a platform formed by integrally joining caps of all of the bioinformation detector units.

* * * * *